United States Patent
Doering

(10) Patent No.: US 10,722,437 B2
(45) Date of Patent: Jul. 28, 2020

(54) COSMETIC AGENTS WITH "IMPROVED PROTECTION AGAINST BODY ODOR"

(71) Applicant: Henkel AG & Co. KGaA, Duesseldorf (DE)

(72) Inventor: Thomas Doering, Dormagen (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 173 days.

(21) Appl. No.: 15/807,588

(22) Filed: Nov. 9, 2017

(65) Prior Publication Data

US 2018/0168971 A1 Jun. 21, 2018

(30) Foreign Application Priority Data

Dec. 20, 2016 (DE) .................. 10 2016 225 562

(51) Int. Cl.
| | | |
|---|---|---|
| *A61K 8/37* | (2006.01) | |
| *A61K 8/04* | (2006.01) | |
| *A61K 8/34* | (2006.01) | |
| *A61Q 15/00* | (2006.01) | |

(52) U.S. Cl.
CPC ............. *A61K 8/37* (2013.01); *A61K 8/046* (2013.01); *A61K 8/342* (2013.01); *A61K 8/345* (2013.01); *A61Q 15/00* (2013.01)

(58) Field of Classification Search
None
See application file for complete search history.

(56) References Cited

U.S. PATENT DOCUMENTS

| | | | | |
|---|---|---|---|---|
| 2003/0068295 | A1* | 4/2003 | Rohde | A61L 9/01 424/76.1 |
| 2009/0123392 | A1* | 5/2009 | Braun | A61K 8/0208 424/47 |
| 2009/0238787 | A1 | 9/2009 | Finke et al. | |
| 2011/0014142 | A1* | 1/2011 | Payne | A61K 8/37 424/65 |
| 2018/0168971 | A1 | 6/2018 | Doering | |

FOREIGN PATENT DOCUMENTS

| | | |
|---|---|---|
| DE | 2656405 A1 | 6/1977 |
| DE | 102012205218 A1 | 10/2013 |
| DE | 102013209460 A1 | 11/2014 |
| DE | 102015225892 A1 | 10/2016 |
| WO | 2016200761 A2 | 12/2016 |

OTHER PUBLICATIONS

Intellectual Property Office, Search Report under Section 17(5) for United Kingdom Patent Application No. GB1719129.7 dated Aug. 1, 2018.

* cited by examiner

*Primary Examiner* — Jake M Vu
(74) *Attorney, Agent, or Firm* — Lorenz & Kopf, LLP

(57) ABSTRACT

The present disclosure relates to cosmetic agents which, in addition to an antiperspirant compound and/or a deodorant active ingredient, contain a combination of special cyclical alcohols and specific menthyl compounds. These agents have a high and long-lasting deodorizing effect. The present disclosure also concerns a cosmetic product containing the cosmetic agent as contemplated herein, as well as at least one propellant. Moreover, the present disclosure relates to the use of agents as contemplated herein for treating body odor, as well as the use of a combination of cyclical alcohol and menthyl compound to increase the odor-inhibiting effect of cosmetic agents.

4 Claims, No Drawings

COSMETIC AGENTS WITH "IMPROVED PROTECTION AGAINST BODY ODOR"

CROSS-REFERENCE TO RELATED APPLICATION

This application claims priority to German Patent Application no. 10 2016 225 562.2, filed Dec. 20, 2016, which is incorporated herein by reference in its entirety.

TECHNICAL FIELD

The present application pertains to cosmetic agents which, in addition to a deodorant active ingredient and/or an antiperspirant compound, contain at least one cyclical alcohol and at least one menthyl compound. Use of the combination of one cyclical alcohol and one menthyl compound creates a synergistic effect with respect to the neutralization of body odor. Consequently, an excellent and long-lasting neutralization of unpleasant body odor can be achieved even without the use of perfume compounds, which can cause allergies.

BACKGROUND

The present disclosure also concerns a cosmetic product containing the cosmetic agent as contemplated herein, as well as at least one propellant.
Moreover, the present disclosure relates to the use of the cosmetic agent as contemplated herein or of the cosmetic product as contemplated herein for reducing the body odor induced by perspiration.

Finally, the present disclosure relates to the use of a mixture of a special alcohol and a menthyl compound for increasing the odor-inhibiting effect of cosmetic agents.

Eccrine and apocrine sweat glands exist in the human armpit. Whereas the eccrine glands produce an aqueous secretion in response to heat, the apocrine glands eliminate a viscous secretion in response to stress. This apocrine sweat constitutes a complex mixture containing, among other constituents, steroids, cholesterol and other fats, as well as approx. 10% of proteins. The bacterial decomposition of the constituents of the apocrine sweat causes the secretion, which is initially odorless, to produce an unpleasant body odor under the armpit.

The decomposition of the apocrine sweat, which contributes substantially to body odor, more particularly to axillary body odor, can be divided into three classes: the first class comprises short-chained $C_4$-$C_{10}$ fatty acids, which can be linear, branched, saturated and unsaturated (for example, isovaleric acid, 3M2H), the second class comprises short-chained, linear or branched sulfonyl alcohols, the third class comprises various steroid hormones and the metabolic products thereof (for example, 5-α-androstenol and 5-α-androstenone).

Accordingly, body odor can be combated by preventing the bacterial decomposition of the sweat or by using perfume to conceal the body odor. In the prior art, the bacterial decomposition of sweat is prevented through the use of antimicrobial substances, which reduce the number of sweat-decomposing bacteria on the skin by employing elimination, or inhibit the growth of said bacteria. However, such substances have the disadvantage that the natural skin flora under the armpit is likewise negatively impacted and can build up resistances to such substances. The use of perfume has the disadvantage that many perfume components, lily aldehyde for example, can induce allergies. This is particularly because a high concentration of the perfume has to be used in order to conceal the unpleasant body odor in a reliable and long-lasting manner. Therefore, there is still a need for active ingredients and/or active ingredient mixtures which have both a high as well as a long-lasting deodorant effect against body odor, and which do not induce any allergies or cause excessive damage to the skin flora.

The present disclosure therefore addressed the problem of providing a cosmetic agent for reducing or preventing body odor which, despite low perfume concentrations or in the absence of perfume, has a good and long-lasting effect against body odor. Moreover, said cosmetic agents are not to have any allergy-inducing potential and should be highly compatible with the skin. In addition, said agents are to be cost-effective to produce and have a long shelf life.

BRIEF SUMMARY

Cosmetic agents and methods of using such agents are provided herein. In an exemplary embodiment, a cosmetic agent comprises, relative to the total weight thereof, at least one alcohol of the Formula (I)

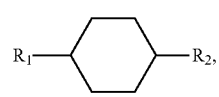

(I)

wherein $R_1$ and $R_2$ denote, independently of one another, hydrogen, a linear $C_2$-$C_{10}$ hydroxyalkyl group or a branched $C_2$-$C_{10}$ hydroxyalkyl group, on condition that $R_1$ and $R_2$ do not both denote hydrogen, at least one menthyl compound of the Formula (II)

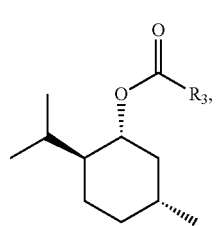

(II)

wherein $R_3$ denotes a $C_1$-$C_4$-alkyl group, a $C_2$-$C_6$ hydroxyalkyl group or a pyrrolidone radical and at least one antiperspirant compound and/or at least one deodorant active ingredient.

In an exemplary embodiment, a method comprises using a mixture of at least one alcohol of the Formula (I)

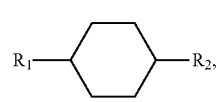

(I)

wherein $R_1$ and $R_2$ denote, independently of one another, hydrogen, a linear $C_2$-$C_{10}$ hydroxyalkyl group or a branched $C_2$-$C_{10}$ hydroxyalkyl group, on condition that $R_1$ and $R_2$ do not both denote hydrogen, at least one menthyl compound of the Formula (II)

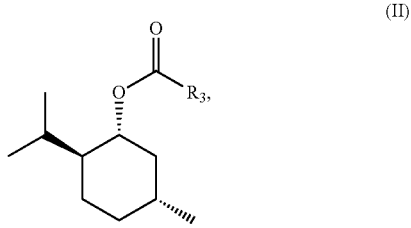
(II)

wherein $R_3$ denotes a $C_1$-$C_4$-alkyl group, a $C_2$-$C_5$ hydroxyalkyl group or a pyrrolidone radical and increases the odor-inhibiting effect of cosmetic agents.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It has now surprisingly emerged that a combination of at least one cyclical alcohol and at least one menthyl compound has a synergistic effect with respect to neutralizing and/or concealing unpleasant body odor.

A first subject matter of the present disclosure is therefore a cosmetic agent containing—relative to its total weight—
a) at least one alcohol of the Formula (I)

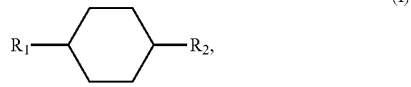
(I)

wherein
$R_1$ and $R_2$ denote, independently of one another, hydrogen, a linear $C_2$-$C_{10}$ hydroxyalkyl group or a branched $C_2$-$C_{10}$ hydroxyalkyl group, on condition that $R_1$ and $R_2$ do not both denote hydrogen,
b) at least one menthyl compound of the Formula (II)

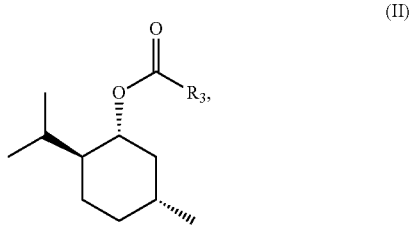
(II)

wherein
$R_3$ denotes a $C_1$-$C_4$-alkyl group, a $C_2$-$C_6$ hydroxyalkyl group or a pyrrolidone radical and c) at least one antiperspirant compound and/or at least one deodorant active ingredient. The use of a mixture of at least one cyclical alcohol of the Formula (I) and at least one menthyl compound of the Formula (II) leads to a synergistic increase in the effect against unpleasant odors over the use of individual components. In this way, a long-lasting deodorizing effect can be achieved even without the use of allergy-inducing perfume constituents and/or the concentration of said components and hence the risk of allergies occurring are reduced.

As contemplated herein, the expression "antiperspirant compound" means reducing and/or avoiding the production of body odor.

Moreover, the term "deodorant active ingredient" according to the present disclosure means a compound having anti-microbial and/or enzyme-inhibiting properties. The cyclical alcohol of the Formula (I), the menthyl compound of the Formula (II), the ethanol used as a cosmetic carrier, as well as the perfume constituents with deodorizing effect, however, are not considered deodorant active ingredients as contemplated herein.

Unless otherwise specified, the wt. % refers in this case to the total weight of the cosmetic agents as contemplated herein, wherein the sum total of all ingredients of the agents as contemplated herein amounts to about 100 wt. %.

The cosmetic agent contains the constituents a) to c) in a cosmetically compatible carrier. Said carrier preferably contains at least one component, selected from water, ethanol, a cosmetic oil that is liquid under normal conditions, as well as mixtures thereof. The cosmetic oils that are liquid under normal conditions are not miscible with water and are neither aromatic substances nor essential oils. According to the present application, "normal conditions" constitute a temperature of 20° C. and a pressure of 1,013 hPa.

Particularly preferred cosmetic carriers are anhydrous carriers. As contemplated herein, anhydrous carriers are those containing less than about 5.0 wt. %, preferably less than about 4.0 wt. %, more preferably less than about 3.0 wt. %, most preferably about 0 wt. %, relative to the total weight of the cosmetic agent, of free water. However, water of crystallization, water of hydration or water with similar molecular bonds of the used constituents, more particularly of the antiperspirant compound, are not included in the calculation of the total amount of free water.

Anhydrous cosmetic carriers preferably contain liquid cosmetic oils. Said cosmetic oils can be selected from the group of (i) volatile non-silicone oils, more particularly liquid paraffin oils and isoparaffin oils, such as isodecane, isoundecane, isododecane, isotridecane, isotetradecane, isopentadecane, isohexadecane and isoeicosane; (ii) non-volatile non-silicone oils, more particularly the carboxylic acid esters and dicarboxylic acid esters of linear or branched $C_2$-$C_{10}$ alkanols, the adducts of ethylene oxide and/or propylene oxide on monovalent or polyvalent $C_3$-$C_{22}$ alkanols, which can in some cases be esterified, the symmetrical, asymmetrical or cyclical esters of the carbonic acids with fatty alcohols, the esters of dimeric unsaturated $C_{12-22}$ fatty acids with monovalent, linear, branched and cyclical $C_{2-18}$ alkanols or $C_{2-6}$ alkanols, the benzoic acid esters of linear or branched $C_{8-22}$ alkanols, such as benzoic acid $C_{12-15}$ alkyl esters and benzoic acid isostearylesters, the synthetic hydrocarbons, such as polyisobutene and polydecene, the alicyclical hydrocarbons; as well as (iii) the mixtures thereof.

As contemplated herein, the expression "liquid cosmetic oil" refers to cosmetic oils which have a vapor pressure of from about 2.66 Pa to about 40,000 Pa (0.02 to 300 mm Hg), preferably from about 10 to about 12,000 Pa (from about 0.1 to about 90 mm Hg), more preferably from about 13 to about 3,000 Pa (from about 0.1 to about 23 mm Hg), most preferably from about 15 to about 500 Pa (from about 0.1 to about 4 mm Hg) at 20° C. and an environmental pressure of 1,013 hPa. Moreover, the expression "non-volatile cosmetic oils" as contemplated herein means oils which have a vapor pressure of less than 2.66 Pa (0.02 mm Hg) at 20° C. and an environmental pressure of 1,013 hPa.

As contemplated herein, the preference is for the use of mixtures of the aforementioned cosmetic oils, particularly non-volatile and volatile cosmetic oils, since this enables parameters such as skin feel, visibility of residue and stability of the cosmetic agent as contemplated herein to be adjusted, thereby allowing the agent to be better adapted to the needs of the consumer.

According to the present disclosure, the cosmetic oil, which is liquid at 20° C. and 1,013 hPa, is ideally contained in a total quantity from about 1.0 to about 98 wt. %, preferably from about 25 to about 80 wt. %, more preferably from about 30 to about 75 wt. %, even more preferably from about 35 to about 70 wt. %, most preferably from about 40 to about 65 wt. %, relative to the total weight of the cosmetic agent.

Other most preferred cosmetic carriers are alcoholic carriers. These contain at least one alcohol with 1 to 4 carbon atoms, ethanol and isopropanol, for example. Alcoholic carriers preferably contain ethanol in a total quantity from about 40 to about 95 wt. %, more preferably from about 45 to about 95 wt. %, most preferably from about 50 to about 95 wt. %, relative to the total weight of the cosmetic agent.

As a first essential constituent a), the cosmetic agent as contemplated herein contains at least one cyclical alcohol of the Formula (I).

As contemplated herein, the preference is for use of cyclical alcohols according to the Formula (I), in which radicals $R_1$ and $R_2$ denote particular groups. Advantageous cosmetic agents as contemplated herein are therefore exemplified in that, in the Formula (I) the radicals $R_1$ and $R_2$ denote, independently of one another, *—H, *—$CH_2$—OH, *—$CH(CH_3)$—OH or *—$(CH_2)_3$—$CH(CH_3)$—$CH_2$—OH, on condition that $R_1$ and $R_2$ do not both denote hydrogen. The bond from radicals $R_1$ and $R_2$ to the cyclohexane is characterized via the symbol *. The use of such cyclical alcohols, more particularly 2-methyl-5-cyclopentanol ($R_1$=H, $R_2$=*—$(CH_2)_3$—$CH(CH_3)$—$CH_2$—OH), 1-cyclohexylethanol ($R_1$=H, $R_2$=*—$CH(CH_3)$—OH) and dimethylolcyclohexane ($R_1$ and $R_2$ both *—$CH_2$—OH), in combination with the at least one menthyl compound of the Formula (II) creates a synergistic effect with respect to the reduction of unpleasant body odor.

As a second essential constituent b), the cosmetic agent as contemplated herein contains at least one menthyl compound of the Formula (II). According to the present disclosure, however, the use of particular menthyl compounds has proven advantageous. It is therefore preferable if, in the Formula (II), the radical $R_3$ denotes *—$CH_3$, *—$CH(OH)$—$CH_3$ or a pyrrolidone radical. The bond from radical $R_3$ to the carbonyl groups is characterized via the symbol *. The use of said menthyl compounds of the Formula (II), more particularly menthylacetate ($R_3$=*—$CH_3$), menthyllactate ($R_3$=*—$CH(OH)$—$CH_3$) and pyroglutamic acid-menthyl ester ($R_3$=pyrrolidone radical), in combination with the at least one cyclical alcohol of the Formula (I), more particularly 2-methyl-5-cyclopentanol ($R_1$=H, $R_2$=*—$(CH_2)_3$—$CH(CH_3)$—$CH_2$—OH), 1-cyclohexylethanol ($R_1$=H, $R_2$=*—$CH(CH_3)$—OH) and dimethylolcyclohexane ($R_1$ and $R_2$ each being *—$CH_2$—OH), creates a synergistic effect with respect to reducing unpleasant body odor. As a result, allergy-inducing perfume constituents need not be used and/or the concentration thereof can be reduced, without any negative impact on the long-lasting deodorizing effect of the cosmetic agents as contemplated herein.

It has surprisingly emerged that a particularly high neutralization of unpleasant body odor can be achieved by using certain combinations of cyclical alcohol of the Formula (I) and menthyl compound of the Formula (II). Therefore, preferred embodiments of the cosmetic agents as contemplated herein are listed below.

A particularly preferred embodiment of the cosmetic agents as contemplated herein is exemplified in that the Formula (I) of radical $R_1$ denotes hydrogen and radical $R_2$ denotes *—$(CH_2)_3$—$CH(CH_3)$—$CH_2$—OH, and in that in the Formula (II), radical $R_3$ denotes *—$CH_3$. Hence, 2-methyl-5-cyclopentanol ($R_1$=H, $R_2$=*—$(CH_2)_3$—$CH(CH_3)$—$CH_2$—OH) is used as the alcohol of the Formula (I), and menthylacetate ($R_3$=*—$CH_3$) as the menthyl compound of the Formula (II).

Moreover, a different and likewise most preferred embodiment of the cosmetic agents as contemplated herein is exemplified in that, in the Formula (I), radical $R_1$ denotes hydrogen and radical $R_2$ denotes*—$CH(CH_3)$—OH and in the Formula (II), radical $R_3$ denotes *—$CH_3$. Hence, 1-cyclohexylethanol ($R_1$=H, $R_2$=*—$CH(CH_3)$—OH) is used as the alcohol of the Formula (I) and menthylacetate ($R_3$=*—$CH_3$) as the menthyl compound of the Formula (II).

Moreover, a different and likewise most preferred embodiment of the cosmetic agents as contemplated herein is exemplified in that, in the Formula (I), radical $R_1$ denotes hydrogen and radical $R_2$ denotes *—$CH(CH_3)$—OH and in the Formula (II), radical $R_3$ denotes *—$CH_3$. Hence, 1-cyclohexylethanol ($R_1$=H, $R_2$=*—$CH(CH_3)$—OH) is used as the alcohol of the Formula (I) and menthyllactate ($R_3$=*—$CH(OH)$—$CH_3$) as the menthyl compound of the Formula (II).

Moreover, a different and likewise most preferred embodiment of the cosmetic agents as contemplated herein is exemplified in that, in the Formula (I), radicals $R_1$ and $R_2$ both denote *—$CH_2$—OH and in the Formula (II), radical $R_3$ denotes *—$CH(OH)$—$CH_3$. Hence, dimethylolcyclohexane ($R_1$ and $R_2$ both*—$CH_2$—OH) is used as the alcohol of the Formula (I) and menthyllactate ($R_3$=*—$CH(OH)$—$CH_3$) as the menthyl compound of the Formula (II).

Finally, a different and likewise most preferred embodiment of the cosmetic agents as contemplated herein is exemplified in that, in the Formula (I), radical $R_1$ denotes hydrogen and radical $R_2$ denotes*—$CH(CH_3)$—OH and in the Formula (II), radical $R_3$ denotes a pyrrolidone radical. Hence, 1-cyclohexylethanol ($R_1$=H, $R_2$=*—$CH(CH_3)$—OH) is used as the alcohol of the Formula (I) and pyroglutamic acid menthylester ($R_3$=pyrrolidone radical) is used as the methyl compound of the Formula (II).

Unlike agents containing only the cyclical alcohol of the Formula (I) or only the menthyl compound of the Formula (II), the aforementioned most preferred embodiments lead to a synergistic neutralization of body odor. Due to this effect, the required quantity of the cyclical alcohol of the Formula (I) and the menthyl compound of the Formula (II) can be reduced without the deodorizing effect being negatively impacted over deodorants of the prior art. In addition, said most preferred compounds have no allergy-inducing potential. Moreover, the slight inherent odor of said compounds, as well as the excellent and long-lasting deodorizing effect thereof, make the use of additional allergenic perfume components to conceal the inherent odor and/or to obtain an adequate deodorizing effect superfluous.

The cyclical alcohol of the Formula (I), more particularly 2-methyl-5-cyclopentanol ($R_1$=H, $R_2$=*—$(CH_2)_3$—$CH(CH_3)$—$CH_2$—OH), 1-cyclohexylethanol ($R_1$=H, $R_2$=*—$CH(CH_3)$—OH) and dimethylolcyclohexane ($R_1$ and $R_2$ both denote *—CH$_2$—OH), are preferably contained in the cosmetic agents as contemplated herein in specific total quantities. As contemplated herein, it is therefore preferable for the at least one alcohol of the Formula (I) to be contained in a total quantity of from about 0.001 to about 0.75 wt. %, more preferable from about 0.001 to about 0.60 wt. %, even more preferable from about 0,0022 to about 0.40 wt. %, most preferable from about 0.003 to about 0.10 wt. %, relative to the total weight of the cosmetic agent. If a mixture of various cyclical alcohols of the Formula (I) is used, said quantity values refer to the total quantity of the mixture of alcohols of the Formula (I). The synergistic effect with respect to the odor neutralization is achieved even at very low quantities of the cyclical alcohol of the Formula (I), more particularly 2-methyl-5-cyclopentanol ($R_1$=H, $R_2$=*—(CH$_2$)$_3$—CH(CH$_3$)—CH$_2$—OH), 1-cyclohexylethanol ($R_1$=H, $R_2$=*—CH(CH$_3$)—OH) and dimethylolcyclohexane ($R_1$ and $R_2$ both denote *—CH$_2$—OH). Due to the slight intrinsic odor of said alcohols in the claimed quantity ranges, the use of additional allergenic perfume components to conceal the intrinsic odor and/or to achieve an adequate deodorizing effect is not absolutely essential.

The menthyl compound of the Formula (II), more particularly menthylacetate ($R_3$=*—CH$_3$), menthyllactate ($R_3$=*—CH(OH)—CH$_3$) and pyroglutamic acid-menthylester ($R_3$=pyrrolidone radical), are also preferably contained in the cosmetic agents as contemplated herein in specific total quantities. As contemplated herein, it is therefore preferable for the at least one menthyl compound of the Formula (II) to be contained in a total quantity of from about 0.1 to about 3.0 wt. %, more preferable from about 0.02 to about 2.0 wt. %, even more preferable from about 0.03 to about 1.0 wt. %, most preferable from about 0.05 to about 0.50 wt. %, relative to the total weight of the cosmetic agent. If a mixture of various menthyl compounds of the Formula (II) is used, said quantity values refer to the total quantity of the mixture of menthyl compounds of the Formula (II). The synergistic effect with respect to the odor neutralization is achieved even at very low quantities of the menthyl compounds of the Formula (II), more particularly menthylacetate ($R_3$=*—CH$_3$), menthyllactate ($R_3$=*—CH(OH)—CH$_3$) and pyroglutamic acid-menthylester ($R_3$=pyrrolidone radical). Due to the slight intrinsic odor of said alcohols in the claimed quantity ranges, the use of additional allergenic perfume components is not absolutely essential.

According to the present disclosure, the use of specific weight ratios of the cyclical alcohol of the Formula (I), more particularly 2-methyl-5-cyclopentanol ($R_1$=H, $R_2$=*—(CH$_2$)$_3$—CH(CH$_3$)—CH$_2$—OH), 1-cyclohexylethanol ($R_1$=H, $R_2$=*—CH(CH$_3$)—OH) and dimethylolcyclohexane ($R_1$ and $R_2$ both denote *—CH$_2$—OH), to the at least one menthyl compound of the Formula (II), more particularly menthylacetate ($R_3$=*—CH$_3$), menthyllactate ($R_3$=*—CH(OH)—CH$_3$) and pyroglutamic acid-menthylester ($R_3$=pyrrolidone radical) has proven particularly advantageous. As contemplated herein, it is therefore preferable for the cosmetic agent to have a weight ratio of the at least one alcohol of the Formula (I) to the at least one menthyl compound of the Formula (II) of from about 75:1 to about 1:300, more preferable of from about 15:1 to about 1:30, even more preferable of from about 2:1 to about 1:20, most preferable of about 1:15. The use of the aforementioned weight ratios achieves a particularly high synergistic effect with respect to the long-lasting neutralization of unpleasant body odors. Moreover, mixtures of the claimed alcohols and menthyl compounds in the aforementioned weight ratios have neither an allergenic potential nor a strong intrinsic odor.

As a third essential constituent c), the cosmetic agent as contemplated herein contains at least one antiperspirant compound and/or at least one deodorant active ingredient. Deodorant active ingredients do not include, however, deodorizing perfume components, deodorizing antiperspirant compounds such as aluminum salts and/or aluminum-zirconium salts, the ethanol used as the carrier, the cyclical alcohol of the Formula (I), or the menthyl compound of the Formula (II).

According to the present disclosure, specific antiperspirant compounds are preferably used. Advantageous embodiments of the cosmetic agents as contemplated herein are therefore exemplified in that the at least one antiperspirant compound is selected from antiperspirant aluminum salts, more particularly aluminum chlorohydrate, and/or antiperspirant aluminum zirconium salts, more particularly aluminum zirconiumtrichlorohydrexglycine and/or aluminum zirconiumtetrachlorohydrexglycine. A most preferred antiperspirant compound is aluminum chlorohydrate.

The at least one antiperspirant compound is preferably contained in the cosmetic agents as contemplated herein in specific total quantities. According to the present disclosure, it is therefore preferable for the at least-one antiperspirant compound, more particularly aluminum chlorohydrate to be contained in a total quantity of from about 10 to about 45 wt. %, more preferable from about 11 to about 40 wt. %, even more preferable from about 12 to about 38 wt. %, most preferable from about 15 to about 35 wt. %, relative to the total weight of the cosmetic agent. The use of the at least one antiperspirant compound in the aforementioned total quantities achieves a good antiperspirant effect, without any negative impact on the synergistic effect with respect to the long-lasting neutralization of unpleasant body odors created by the cyclical alcohol of the Formula (I) and the menthyl compound of the Formula (II).

As contemplated herein, the use of specific compounds as deodorant active ingredients can also be advantageous. As contemplated herein, it is therefore preferable for the at least one deodorant active ingredient to be selected from the group of (i) arylsulfatase inhibitors, beta-glucuronidase inhibitors, aminoacylase inhibitors, esterase inhibitors, lipase inhibitors and lipoxigenase inhibitors; (ii) α-monoalkylglycerinethern with a branched or linear saturated or unsaturated, if necessary hydroxylated $C_6$-$C_{22}$-alkyl radical, more particularly α-(2-ethylhexyl)glycerinether, (iii) alcohols, more particularly phenoxyethanol, benzylheptanol, 1,2-hexandiol, 1,2-octanediol, 1,2-decanediol, tropolone and butyloctanoic acid; (iv) germicidal perfume oils; (v) prebiotically effective components; (vi) trialkyl citric acid esters, more particularly triethylcitrate; (vii) active ingredients, which reduce the number of skin flora involved in the production of odor from the group of staphylococci, corynebacteria, anaerococci and micrococci and/or inhibit the growth thereof, (viii) zinc and silver compounds, more particularly zinc phenolsulfonate, zincricinoleate, bischloride(-1)-octahydroxy-pentazinc, zinc zitrate and silver lactate; (ix) organohalogen compounds, more particularly triclosane, chlorhexidine and chlorhexidine gluconate; (x) benzalkonium halides, more particularly benzalkonium chloride and benzethoniumchloride; (xi) quarternary ammonium compounds, more particularly cetylpyridiniumchloride; (xii) antimicrobially effective carbonates, phosphates and sulphates, more particularly sodium bicarbonate, cocamidopropyl PG-dimonium chloride phosphate, di-sodium pyrophosphate and soya morpholinium ethosulfate; (xiii) lantibiotics; (xiv) bispyridinene, more particularly octenidine; (xv) antimicrobially effective acids, more particularly caprylhydroxamic acid, carnesolic acid and tartaric acid; (xvi) polyglycerinester; (xvii) sorbitan esters and lactones, more particularly sorbitancaprylate and glucono-1,5-lactone; (xviii) as well as the mixtures thereof. The synergistic increase in the deodorizing effect achieved by the mixture of a cyclical alcohol of the Formula (I), more particularly 2-methyl-5-cyclopentanol ($R_1$=H, $R_2$=*—$(CH_2)_3$—$CH(CH_3)$—$CH_2$—OH), 1-cyclohexylethanol ($R_1$=H, $R_2$=*—$CH(CH_3)$—OH) and dimethylolcyclohexane ($R_1$ and $R_2$ both denote *—$CH_2$—OH), and a menthyl compound of the Formula (II), more particularly menthylacetate ($R_3$=*—$CH_3$), menthyllactate ($R_3$=*—CH(OH)—$CH_3$) and pyroglutamic acid-menthyl ester ($R_3$=pyrrolidone radical) can be further improved by using triethyl citrate and/or phenoxyethanol and/oder α-(2-ethylhexyl)glycerin ether is used as the deodorant active ingredient.

According to the present disclosure, the use of the at least one deodorant active ingredient, more particularly triethyl citrate and/or phenoxyethanol and/or α-(2-ethylhexyl) glycerin ether in a specific total quantity can be preferred. Preferred embodiments of the cosmetic agents as contemplated herein are therefore exemplified in that the at least one deodorant active ingredient, more particularly triethyl citrate and/or phenoxyethanol and/oder α-(2-ethylhexyl) glycerin ether is contained in a total quantity from about 0.0001 to about 15 wt. %, preferably from about 0.001 to about 15 wt. %, more preferably from about 0.01 to about 15 wt. %, most preferably from about 0.5 to about 15 wt. %, relative to the total weight of the cosmetic agent in each case. The use of the at least one deodorant active ingredient, more particularly of triethyl citrate and/or phenoxyethanol and/or α-(2-ethylhexyl)glycerin ether, in the aforementioned total quantities achieves a further improvement of the synergistic neutralization of unpleasant body odors created by the combination of a cyclical alcohol of the Formula (I), more particularly 2-methyl-5-cyclopentanol ($R_1$=H, $R_2$=*—$(CH_2)_3$—$CH(CH_3)$—$CH_2$—OH), 1-cyclohexylethanol ($R_1$=H, $R_2$=*—$CH(CH_3)$—OH) and Dimethylolcyclohexane ($R_1$ and $R_2$ both denote*—$CH_2$—OH), and menthyl compound of the Formula (II), more particularly menthylacetate ($R_3$=*—$CH_3$), menthyllactate ($R_3$=*—CH(OH)—$CH_3$) and pyroglutamic acid-menthylester ($R_3$=pyrrolidone radical). Moreover, the effect achieved by employing the deodorant active ingredient in the aforementioned total quantities can be extended.

The cosmetic agents as contemplated herein are preferably deodorant compositions. As contemplated herein, it is therefore advantageous for the cosmetic agent to be free of antiperspirant compounds. Hence, deodorants according to the present disclosure contain 0 wt. %, relative to the total weight of the cosmetic agent, of antiperspirant compounds.

According to the present disclosure, is also preferable for the cosmetic agent to contain, apart from the cyclical alcohol of the Formula (I) and the menthyl compound of the Formula (II), no perfume components, more particularly no allergy-inducing perfume components. Advantageous embodiments of the cosmetic agents as contemplated herein are exemplified in that they contain no additional scents or the mixtures thereof. As contemplated herein, scents are substances with a molecular weight from about 74 to about 300 g/mol, which contain at least one osmophore group in the molecule and have an odor and/or a flavor, i.e. are able to excite the receptors of the hair cells in the olfactory system. Osmophore groups are groups that are covalently bonded to the molecular structure in the form of hydroxy groups, formyl groups, oxo groups, alkoxycarbonyl groups, nitrile groups, nitro groups, azide groups, etc. In this connection, the term "scents" as contemplated herein also encompasses perfume oils, perfumes or perfume oil constituents that are liquid at 20° C. and 1.013 hPa. Said term, however, does not encompass alcohols of the Formula (I) and the menthyl compound of the Formula (II). Preferred cosmetic agents therefore contain 0 wt. % of additional scents and scent mixtures.

In addition to the aforementioned essential constituents a) to c), the cosmetic agent as contemplated hereincan also contain at least one thickening agent. Preferred cosmetic agents therefore contain in addition at least one thickening agent, selected from the group of (i) hydrophobized clay minerals: (ii) Bentonites; (iii) pyrogenic silicas; (iv) talcum; as well as (vii) the mixtures thereof, more particularly bentonites. The at least one thickening agent, more particularly hydrophobized clay minerals, is preferably contained in a total quantity from about 0.1 to about 5.5 wt. %, more preferably from about 0.5 to about 5.0 wt. %, even more preferably from about 1.0 to about 4.0 wt. %, most preferably from about 1.5 to about 3.5 wt. %, relative to the total weight of the anhydrous cosmetic agent.

The table below shows most preferred embodiments AF 1 to AF 156 of the cosmetic agent as contemplated herein (all value in wt. %). These agents preferably contain no additional scents and/or the mixtures thereof. The embodiments AF5-8, AF17-20, AF29-32, AF41-44, AF53-56, AF65-68, AF77-80 AF89-92, AF101-104, AF113-116, AF125-128, AF137-140, as well as AF149-152, also preferably contain 0 wt. %, relative to the total weight of the embodiment concerned, of antiperspirant compounds.

|  | AF 1 | AF 2 | AF 3 | AF 4 |
|---|---|---|---|---|
| Cyclical alcohol of the Formula (I) | 0.001-0.75 | 0.001-0.60 | 0.0022-0.40 | 0.003-0.10 |
| Menthyl compound of the Formula (II) | 0.01-3.0 | 0.02-2.0 | 0.03-1.0 | 0.05-0.50 |
| Antiperspirant compound | 10-45 | 11-40 | 12-38 | 15-35 |
| Cosmetic carrier | ad 100 | ad 100 | ad 100 | ad 100 |
|  | AF 5 | AF 6 | AF 7 | AF 8 |
| Cyclical alcohol of the Formula (I) | 0.001-0.75 | 0.001-0.60 | 0.0022-0.40 | 0.003-0.10 |
| Menthyl compound of the Formula (II) | 0.01-3.0 | 0.02-2.0 | 0.03-1.0 | 0.05-0.50 |
| Deodorant active ingredient | 0.0001-15 | 0.001-15 | 0.01-15 | 0.5-15 |
| Cosmetic carrier | ad 100 | ad 100 | ad 100 | ad 100 |

-continued

|  | AF 9 | AF 10 | AF 11 | AF 12 |
|---|---|---|---|---|
| Cyclical alcohol of the Formula (I) | 0.001-0.75 | 0.001-0.60 | 0.0022-0.40 | 0.003-0.10 |
| Menthyl compound of the Formula (II) | 0.01-3.0 | 0.02-2.0 | 0.03-1.0 | 0.05-0.50 |
| Antiperspirant compound | 10-45 | 11-40 | 12-38 | 15-35 |
| Deodorant active ingredient | 0.0001-15 | 0.001-15 | 0.01-15 | 0.5-15 |
| Cosmetic carrier | ad 100 | ad 100 | ad 100 | ad 100 |

|  | AF 13 | AF 14 | AF 15 | AF 16 |
|---|---|---|---|---|
| Cyclical alcohol of the Formula (I)[1] | 0.001-0.75 | 0.001-0.60 | 0.0022-0.40 | 0.003-0.10 |
| Menthyl compound of the Formula (II)[2] | 0.01-3.0 | 0.02-2.0 | 0.03-1.0 | 0.05-0.50 |
| Antiperspirant compound | 10-45 | 11-40 | 12-38 | 15-35 |
| Cosmetic carrier | ad 100 | ad 100 | ad 100 | ad 100 |

|  | AF 17 | AF 18 | AF 19 | AF 20 |
|---|---|---|---|---|
| Cyclical alcohol of the Formula (I)[1] | 0.001-0.75 | 0.001-0.60 | 0.0022-0.40 | 0.003-0.10 |
| Menthyl compound of the Formula (II)[2] | 0.01-3.0 | 0.02-2.0 | 0.03-1.0 | 0.05-0.50 |
| Deodorant active ingredient | 0.0001-15 | 0.001-15 | 0.01-15 | 0.5-15 |
| Cosmetic carrier | ad 100 | ad 100 | ad 100 | ad 100 |

|  | AF 21 | AF 22 | AF 23 | AF 24 |
|---|---|---|---|---|
| Cyclical alcohol of the Formula (I)[1] | 0.001-0.75 | 0.001-0.60 | 0.0022-0.40 | 0.003-0.10 |
| Menthyl compound of the Formula (II)[2] | 0.01-3.0 | 0.02-2.0 | 0.03-1.0 | 0.05-0.50 |
| Antiperspirant compound | 10-45 | 11-40 | 12-38 | 15-35 |
| Deodorant active ingredient | 0.0001-15 | 0.001-15 | 0.01-15 | 0.5-15 |
| Cosmetic carrier | ad 100 | ad 100 | ad 100 | ad 100 |

|  | AF 25 | AF 26 | AF 27 | AF 28 |
|---|---|---|---|---|
| Cyclical alcohol of the Formula (I)[3] | 0.001-0.75 | 0.001-0.60 | 0.0022-0.40 | 0.003-0.10 |
| Menthyl compound of the Formula (II)[4] | 0.01-3.0 | 0.02-2.0 | 0.03-1.0 | 0.05-0.50 |
| Antiperspirant compound | 10-45 | 11-40 | 12-38 | 15-35 |
| Cosmetic carrier | ad 100 | ad 100 | ad 100 | ad 100 |

|  | AF 29 | AF 30 | AF 31 | AF 32 |
|---|---|---|---|---|
| Cyclical alcohol of the Formula (I)[3] | 0.001-0.75 | 0.001-0.60 | 0.0022-0.40 | 0.003-0.10 |
| Menthyl compound of the Formula (II)[4] | 0.01-3.0 | 0.02-2.0 | 0.03-1.0 | 0.05-0.50 |
| Deodorant active ingredient | 0.0001-15 | 0.001-15 | 0.01-15 | 0.5-15 |
| Cosmetic carrier | ad 100 | ad 100 | ad 100 | ad 100 |

|  | AF 33 | AF 34 | AF 35 | AF 36 |
|---|---|---|---|---|
| Cyclical alcohol of the Formula (I)[3] | 0.001-0.75 | 0.001-0.60 | 0.0022-0.40 | 0.003-0.10 |
| Menthyl compound of the Formula (II)[4] | 0.01-3.0 | 0.02-2.0 | 0.03-1.0 | 0.05-0.50 |
| Antiperspirant compound | 10-45 | 11-40 | 12-38 | 15-35 |
| Deodorant active ingredient | 0.0001-15 | 0.001-15 | 0.01-15 | 0.5-15 |
| Cosmetic carrier | ad 100 | ad 100 | ad 100 | ad 100 |

|  | AF 37 | AF 38 | AF 39 | AF 40 |
|---|---|---|---|---|
| Cyclical alcohol of the Formula (I)[5] | 0.001-0.75 | 0.001-0.60 | 0.0022-0.40 | 0.003-0.10 |
| Menthyl compound of the Formula (II)[4] | 0.01-3.0 | 0.02-2.0 | 0.03-1.0 | 0.05-0.50 |
| Antiperspirant compound | 10-45 | 11-40 | 12-38 | 15-35 |
| Cosmetic carrier | ad 100 | ad 100 | ad 100 | ad 100 |

|  | AF 41 | AF 42 | AF 43 | AF 44 |
|---|---|---|---|---|
| Cyclical alcohol of the Formula (I)[5] | 0.001-0.75 | 0.001-0.60 | 0.0022-0.40 | 0.003-0.10 |
| Menthyl compound of the Formula (II)[4] | 0.01-3.0 | 0.02-2.0 | 0.03-1.0 | 0.05-0.50 |
| Deodorant active ingredient | 0.0001-15 | 0.001-15 | 0.01-15 | 0.5-15 |
| Cosmetic carrier | ad 100 | ad 100 | ad 100 | ad 100 |

-continued

|  | AF 45 | AF 46 | AF 47 | AF 48 |
|---|---|---|---|---|
| Cyclical alcohol of the Formula (I)[5)] | 0.001-0.75 | 0.001-0.60 | 0.0022-0.40 | 0.003-0.10 |
| Menthyl compound of the Formula (II)[4)] | 0.01-3.0 | 0.02-2.0 | 0.03-1.0 | 0.05-0.50 |
| Antiperspirant compound | 10-45 | 11-40 | 12-38 | 15-35 |
| Deodorant active ingredient | 0.0001-15 | 0.001-15 | 0.01-15 | 0.5-15 |
| Cosmetic carrier | ad 100 | ad 100 | ad 100 | ad 100 |

|  | AF 49 | AF 50 | AF 51 | AF 52 |
|---|---|---|---|---|
| Cyclical alcohol of the Formula (I)[5)] | 0.001-0.75 | 0.001-0.60 | 0.0022-0.40 | 0.003-0.10 |
| Menthyl compound of the Formula (II)[6)] | 0.01-3.0 | 0.02-2.0 | 0.03-1.0 | 0.05-0.50 |
| Antiperspirant compound | 10-45 | 11-40 | 12-38 | 15-35 |
| Cosmetic carrier | ad 100 | ad 100 | ad 100 | ad 100 |

|  | AF 53 | AF 54 | AF 55 | AF 56 |
|---|---|---|---|---|
| Cyclical alcohol of the Formula (I)[5)] | 0.001-0.75 | 0.001-0.60 | 0.0022-0.40 | 0.003-0.10 |
| Menthyl compound of the Formula (II)[6)] | 0.01-3.0 | 0.02-2.0 | 0.03-1.0 | 0.05-0.50 |
| Deodorant active ingredient | 0.0001-15 | 0.001-15 | 0.01-15 | 0.5-15 |
| Cosmetic carrier | ad 100 | ad 100 | ad 100 | ad 100 |

|  | AF 57 | AF 58 | AF 59 | AF 60 |
|---|---|---|---|---|
| Cyclical alcohol of the Formula (I)[5)] | 0.001-0.75 | 0.001-0.60 | 0.0022-0.40 | 0.003-0.10 |
| Menthyl compound of the Formula (II)[6)] | 0.01-3.0 | 0.02-2.0 | 0.03-1.0 | 0.05-0.50 |
| Antiperspirant compound | 10-45 | 11-40 | 12-38 | 15-35 |
| Deodorant active ingredient | 0.0001-15 | 0.001-15 | 0.01-15 | 0.5-15 |
| Cosmetic carrier | ad 100 | ad 100 | ad 100 | ad 100 |

|  | AF 61 | AF 62 | AF 63 | AF 64 |
|---|---|---|---|---|
| Cyclical alcohol of the Formula (I)[7)] | 0.001-0.75 | 0.001-0.60 | 0.0022-0.40 | 0.003-0.10 |
| Menthyl compound of the Formula (II) 6) | 0.01-3.0 | 0.02-2.0 | 0.03-1.0 | 0.05-0.50 |
| Antiperspirant compound | 10-45 | 11-40 | 12-38 | 15-35 |
| Cosmetic carrier | ad 100 | ad 100 | ad 100 | ad 100 |

|  | AF 65 | AF 66 | AF 67 | AF 68 |
|---|---|---|---|---|
| Cyclical alcohol of the Formula (I)[7)] | 0.001-0.75 | 0.001-0.60 | 0.0022-0.40 | 0.003-0.10 |
| Menthyl compound of the Formula (II) 6) | 0.01-3.0 | 0.02-2.0 | 0.03-1.0 | 0.05-0.50 |
| Deodorant active ingredient | 0.0001-15 | 0.001-15 | 0.01-15 | 0.5-15 |
| Cosmetic carrier | ad 100 | ad 100 | ad 100 | ad 100 |

|  | AF 69 | AF 70 | AF 71 | AF 72 |
|---|---|---|---|---|
| Cyclical alcohol of the Formula (I)[7)] | 0.001-0.75 | 0.001-0.60 | 0.0022-0.40 | 0.003-0.10 |
| Menthyl compound of the Formula (II) 6) | 0.01-3.0 | 0.02-2.0 | 0.03-1.0 | 0.05-0.50 |
| Antiperspirant compound | 10-45 | 11-40 | 12-38 | 15-35 |
| Deodorant active ingredient | 0.0001-15 | 0.001-15 | 0.01-15 | 0.5-15 |
| Cosmetic carrier | ad 100 | ad 100 | ad 100 | ad 100 |

|  | AF 73 | AF 74 | AF 75 | AF 76 |
|---|---|---|---|---|
| Cyclical alcohol of the Formula (I)[5)] | 0.001-0.75 | 0.001-0.60 | 0.0022-0.40 | 0.003-0.10 |
| Menthyl compound of the Formula (II)[8)] | 0.01-3.0 | 0.02-2.0 | 0.03-1.0 | 0.05-0.50 |
| Antiperspirant compound | 10-45 | 11-40 | 12-38 | 15-35 |
| Cosmetic carrier | ad 100 | ad 100 | ad 100 | ad 100 |

|  | AF 77 | AF 78 | AF 79 | AF 80 |
|---|---|---|---|---|
| Cyclical alcohol of the Formula (I)[5)] | 0.001-0.75 | 0.001-0.60 | 0.0022-0.40 | 0.003-0.10 |
| Menthyl compound of the Formula (II)[8)] | 0.01-3.0 | 0.02-2.0 | 0.03-1.0 | 0.05-0.50 |
| Deodorant active ingredient | 0.0001-15 | 0.001-15 | 0.01-15 | 0.5-15 |
| Cosmetic carrier | ad 100 | ad 100 | ad 100 | ad 100 |

|  | AF 81 | AF 82 | AF 83 | AF 84 |
|---|---|---|---|---|
| Cyclical alcohol of the Formula (I)[5)] | 0.001-0.75 | 0.001-0.60 | 0.0022-0.40 | 0.003-0.10 |
| Menthyl compound of the Formula (II)[8)] | 0.01-3.0 | 0.02-2.0 | 0.03-1.0 | 0.05-0.50 |
| Antiperspirant compound | 10-45 | 11-40 | 12-38 | 15-35 |
| Deodorant active ingredient | 0.0001-15 | 0.001-15 | 0.01-15 | 0.5-15 |
| Cosmetic carrier | ad 100 | ad 100 | ad 100 | ad 100 |

|  | AF 85 | AF 86 | AF 87 | AF 88 |
|---|---|---|---|---|
| Cyclical alcohol of the Formula (I)[1)] | 0.001-0.75 | 0.001-0.60 | 0.0022-0.40 | 0.003-0.10 |
| Menthyl compound of the Formula (II)[2)] | 0.01-3.0 | 0.02-2.0 | 0.03-1.0 | 0.05-0.50 |
| Antiperspirant compound[9)] | 10-45 | 11-40 | 12-38 | 15-35 |
| Cosmetic carrier | ad 100 | ad 100 | ad 100 | ad 100 |

|  | AF 89 | AF 90 | AF 90 | AF 92 |
|---|---|---|---|---|
| Cyclical alcohol of the Formula (I)[1)] | 0.001-0.75 | 0.001-0.60 | 0.0022-0.40 | 0.003-0.10 |
| Menthyl compound of the Formula (II)[2)] | 0.01-3.0 | 0.02-2.0 | 0.03-1.0 | 0.05-0.50 |
| Deodorant active ingredient[10)] | 0.0001-15 | 0.001-15 | 0.01-15 | 0.5-15 |
| Cosmetic carrier | ad 100 | ad 100 | ad 100 | ad 100 |

|  | AF 93 | AF 94 | AF 95 | AF 96 |
|---|---|---|---|---|
| Cyclical alcohol of the Formula (I)[1)] | 0.001-0.75 | 0.001-0.60 | 0.0022-0.40 | 0.003-0.10 |
| Menthyl compound of the Formula (II)[2)] | 0.01-3.0 | 0.02-2.0 | 0.03-1.0 | 0.05-0.50 |
| Antiperspirant compound[9)] | 10-45 | 11-40 | 12-38 | 15-35 |
| Deodorant active ingredient[10)] | 0.0001-15 | 0.001-15 | 0.01-15 | 0.5-15 |
| Cosmetic carrier | ad 100 | ad 100 | ad 100 | ad 100 |

|  | AF 97 | AF 98 | AF 99 | AF 100 |
|---|---|---|---|---|
| Cyclical alcohol of the Formula (I)[3)] | 0.001-0.75 | 0.001-0.60 | 0.0022-0.40 | 0.003-0.10 |
| Menthyl compound of the Formula (II)[4)] | 0.01-3.0 | 0.02-2.0 | 0.03-1.0 | 0.05-0.50 |
| Antiperspirant compound[9)] | 10-45 | 11-40 | 12-38 | 15-35 |
| Cosmetic carrier | ad 100 | ad 100 | ad 100 | ad 100 |

|  | AF 101 | AF 102 | AF 103 | AF 104 |
|---|---|---|---|---|
| Cyclical alcohol of the Formula (I)[3)] | 0.001-0.75 | 0.001-0.60 | 0.0022-0.40 | 0.003-0.10 |
| Menthyl compound of the Formula (II)[4)] | 0.01-3.0 | 0.02-2.0 | 0.03-1.0 | 0.05-0.50 |
| Deodorant active ingredient[10)] | 0.0001-15 | 0.001-15 | 0.01-15 | 0.5-15 |
| Cosmetic carrier | ad 100 | ad 100 | ad 100 | ad 100 |

|  | AF 105 | AF 106 | AF 107 | AF 108 |
|---|---|---|---|---|
| Cyclical alcohol of the Formula (I)[3)] | 0.001-0.75 | 0.001-0.60 | 0.0022-0.40 | 0.003-0.10 |
| Menthyl compound of the Formula (II)[4)] | 0.01-3.0 | 0.02-2.0 | 0.03-1.0 | 0.05-0.50 |
| Antiperspirant compound[9)] | 10-45 | 11-40 | 12-38 | 15-35 |
| Deodorant active ingredient[10)] | 0.0001-15 | 0.001-15 | 0.01-15 | 0.5-15 |
| Cosmetic carrier | ad 100 | ad 100 | ad 100 | ad 100 |

|  | AF 109 | AF 110 | AF 111 | AF 112 |
|---|---|---|---|---|
| Cyclical alcohol of the Formula (I)[5)] | 0.001-0.75 | 0.001-0.60 | 0.0022-0.40 | 0.003-0.10 |
| Menthyl compound of the Formula (II)[4)] | 0.01-3.0 | 0.02-2.0 | 0.03-1.0 | 0.05-0.50 |
| Antiperspirant compound[9)] | 10-45 | 11-40 | 12-38 | 15-35 |
| Cosmetic carrier | ad 100 | ad 100 | ad 100 | ad 100 |

|  | AF 113 | AF 114 | AF 115 | AF 116 |
|---|---|---|---|---|
| Cyclical alcohol of the Formula (I)[5)] | 0.001-0.75 | 0.001-0.60 | 0.0022-0.40 | 0.003-0.10 |
| Menthyl compound of the Formula (II)[4)] | 0.01-3.0 | 0.02-2.0 | 0.03-1.0 | 0.05-0.50 |
| Deodorant active ingredient[10)] | 0.0001-15 | 0.001-15 | 0.01-15 | 0.5-15 |
| Cosmetic carrier | ad 100 | ad 100 | ad 100 | ad 100 |

-continued

|  | AF 117 | AF 118 | AF 119 | AF 120 |
|---|---|---|---|---|
| Cyclical alcohol of the Formula (I)[5] | 0.001-0.75 | 0.001-0.60 | 0.0022-0.40 | 0.003-0.10 |
| Menthyl compound of the Formula (II)[4] | 0.01-3.0 | 0.02-2.0 | 0.03-1.0 | 0.05-0.50 |
| Antiperspirant compound[9] | 10-45 | 11-40 | 12-38 | 15-35 |
| Deodorant active ingredient[10] | 0.0001-15 | 0.001-15 | 0.01-15 | 0.5-15 |
| Cosmetic carrier | ad 100 | ad 100 | ad 100 | ad 100 |

|  | AF 121 | AF 122 | AF 123 | AF 124 |
|---|---|---|---|---|
| Cyclical alcohol of the Formula (I)[5] | 0.001-0.75 | 0.001-0.60 | 0.0022-0.40 | 0.003-0.10 |
| Menthyl compound of the Formula (II) 6) | 0.01-3.0 | 0.02-2.0 | 0.03-1.0 | 0.05-0.50 |
| Antiperspirant compound[9] | 10-45 | 11-40 | 12-38 | 15-35 |
| Cosmetic carrier | ad 100 | ad 100 | ad 100 | ad 100 |

|  | AF 125 | AF 126 | AF 127 | AF 128 |
|---|---|---|---|---|
| Cyclical alcohol of the Formula (I)[5] | 0.001-0.75 | 0.001-0.60 | 0.0022-0.40 | 0.003-0.10 |
| Menthyl compound of the Formula (II) 6) | 0.01-3.0 | 0.02-2.0 | 0.03-1.0 | 0.05-0.50 |
| Deodorant active ingredient[10] | 0.0001-15 | 0.001-15 | 0.01-15 | 0.5-15 |
| Cosmetic carrier | ad 100 | ad 100 | ad 100 | ad 100 |

|  | AF 129 | AF 130 | AF 131 | AF 132 |
|---|---|---|---|---|
| Cyclical alcohol of the Formula (I)[5] | 0.001-0.75 | 0.001-0.60 | 0.0022-0.40 | 0.003-0.10 |
| Menthyl compound of the Formula (II) 6) | 0.01-3.0 | 0.02-2.0 | 0.03-1.0 | 0.05-0.50 |
| Antiperspirant compound[9] | 10-45 | 11-40 | 12-38 | 15-35 |
| Deodorant active ingredient[10] | 0.0001-15 | 0.001-15 | 0.01-15 | 0.5-15 |
| Cosmetic carrier | ad 100 | ad 100 | ad 100 | ad 100 |

|  | AF 133 | AF 134 | AF 135 | AF 136 |
|---|---|---|---|---|
| Cyclical alcohol of the Formula (I)[7] | 0.001-0.75 | 0.001-0.60 | 0.0022-0.40 | 0.003-0.10 |
| Menthyl compound of the Formula (II) 6) | 0.01-3.0 | 0.02-2.0 | 0.03-1.0 | 0.05-0.50 |
| Antiperspirant compound[9] | 10-45 | 11-40 | 12-38 | 15-35 |
| Cosmetic carrier | ad 100 | ad 100 | ad 100 | ad 100 |

|  | AF 137 | AF 138 | AF 139 | AF 140 |
|---|---|---|---|---|
| Cyclical alcohol of the Formula (I)[7] | 0.001-0.75 | 0.001-0.60 | 0.0022-0.40 | 0.003-0.10 |
| Menthyl compound of the Formula (II) 6) | 0.01-3.0 | 0.02-2.0 | 0.03-1.0 | 0.05-0.50 |
| Deodorant active ingredient[10] | 0.0001-15 | 0.001-15 | 0.01-15 | 0.5-15 |
| Cosmetic carrier | ad 100 | ad 100 | ad 100 | ad 100 |

|  | AF 141 | AF 142 | AF 143 | AF 144 |
|---|---|---|---|---|
| Cyclical alcohol of the Formula (I)[7] | 0.001-0.75 | 0.001-0.60 | 0.0022-0.40 | 0.003-0.10 |
| Menthyl compound of the Formula (II) 6) | 0.01-3.0 | 0.02-2.0 | 0.03-1.0 | 0.05-0.50 |
| Antiperspirant compound[9] | 10-45 | 11-40 | 12-38 | 15-35 |
| Deodorant active ingredient[10] | 0.0001-15 | 0.001-15 | 0.01-15 | 0.5-15 |
| Cosmetic carrier | ad 100 | ad 100 | ad 100 | ad 100 |

|  | AF 145 | AF 146 | AF 147 | AF 148 |
|---|---|---|---|---|
| Cyclical alcohol of the Formula (I)[5] | 0.001-0.75 | 0.001-0.60 | 0.0022-0.40 | 0.003-0.10 |
| Menthyl compound of the Formula (II)[8] | 0.01-3.0 | 0.02-2.0 | 0.03-1.0 | 0.05-0.50 |
| Antiperspirant compound[9] | 10-45 | 11-40 | 12-38 | 15-35 |
| Cosmetic carrier | ad 100 | ad 100 | ad 100 | ad 100 |

|  | AF 149 | AF 150 | AF 151 | AF 152 |
|---|---|---|---|---|
| Cyclical alcohol of the Formula (I)[5] | 0.001-0.75 | 0.001-0.60 | 0.0022-0.40 | 0.003-0.10 |
| Menthyl compound of the Formula (II)[8] | 0.01-3.0 | 0.02-2.0 | 0.03-1.0 | 0.05-0.50 |
| Deodorant active ingredient[10] | 0.0001-15 | 0.001-15 | 0.01-15 | 0.5-15 |
| Cosmetic carrier | ad 100 | ad 100 | ad 100 | ad 100 |

-continued

|  | AF 153 | AF 154 | AF 155 | AF 156 |
|---|---|---|---|---|
| Cyclical alcohol of the Formula (I)[5)] | 0.001-0.75 | 0.001-0.60 | 0.0022-0.40 | 0.003-0.10 |
| Menthyl compound of the Formula (II)[8)] | 0.01-3.0 | 0.02-2.0 | 0.03-1.0 | 0.05-0.50 |
| Antiperspirant compound[9)] | 10-45 | 11-40 | 12-38 | 15-35 |
| Deodorant active ingredient[10)] | 0.0001-15 | 0.001-15 | 0.01-15 | 0.5-15 |
| Cosmetic carrier | ad 100 | ad 100 | ad 100 | ad 100 |

[1)]Radicals $R_1$ and $R_2$ denote, independently of one another, *—H, *—CH$_2$—OH, *—CH(CH$_3$)—OH or *(CH$_2$)$_3$—CH(CH$_3$)—CH$_2$—OH, on condition that $R_1$ and $R_2$ do not both denote nitrogen,
[2)]Radical $R_3$ denotes *—CH$_3$, *—CH(OH)—CH$_3$ or a pyrrolidone radical,
[3)]Radical $R_1$ denotes hydrogen, radical $R_2$ denotes *—(CH$_2$)$_3$—CH(CH$_3$)—CH$_2$—OH,
[4)]Radical $R_3$ denotes *—CH$_3$
[5)]Radical $R_1$ denotes hydrogen and radical $R_2$ denotes *—CH(CH$_3$)—OH,
[6)]Radical $R_3$ denotes *—CH(OH)—CH$_3$,
[7)]Radicals $R_1$ and $R_2$ both denote *—CH$_2$—OH,
[8)]Radical $R_3$ denotes a pyrrolidone radical,
[9)]Aluminum chlorohydrate
[10)]Triethyl citrate and/or phenoxyethanol and/or α-(2-ethylhexyl) glycerin ether.

The aforementioned embodiments 1 to 156 of the cosmetic agents as contemplated herein achieve, through the use of a combination of special cyclical alcohols of the Formula (I), more particularly 2-methyl-5-cyclopentanol ($R_1$=H, $R_2$=*—(CH$_2$)$_3$—CH (CH$_3$)—CH$_2$—OH), 1-cyclohexylethanol ($R_1$=H, $R_2$=*—CH(CH$_3$)—OH) and Dimethylolcyclohexane ($R_1$ and $R_2$ both denote *—CH$_2$—OH), and special menthyl compounds of the Formula (II), more particularly menthylacetate ($R_3$=*—CH$_3$), menthyllactate ($R_3$=*—CH(OH)—CH$_3$) and pyroglutamic acid-menthyl ester ($R_3$=pyrrolidone radical), a synergistic increase of the deodorizing effect compared to the use of individual components. Moreover, the use of said combination can prolong the deodorizing effect. In addition, said compounds in the required total quantities do not have any unpleasant intrinsic odor, which has to be concealed by employing allergenic perfume components. Therefore, said embodiments have both an excellent deodorizing effect and also a low and/or no allergenic potential.

Formulation of the antiperspirant agent as contemplated herein in a specific dosage form, such as a roll-on, a stick or a gel is preferably based on the requirements of the intended use. Therefore, depending on the intended use, the agents as contemplated herein can exist in solid, semi-solid, liquid, dispersed, emulsified, suspended, gelatinous, multi-phase or powder form. According to the present disclosure, the term liquid also encompasses any types of solid-state dispersions in liquids. Moreover, multi-phase antiperspirant agents as contemplated herein are agents which have at least 2 different phases with a phase separation, and wherein the phases can be arranged horizontally, i.e. one above the other, or vertically, i.e. next to one another. Such agents can be applied in the form of a solid stick, soft solid, creme, roll-on, dibenzylidenalditol-based gel, loose or compact powder, for example.

Creme-like, gelatinous, pasty and liquid agents as contemplated herein can be packaged, for example, in the form of pump, spray or squeeze dispensers, more particularly also in the form of multi-chamber pump, multi-chamber spray or multi-chamber squeeze dispensers. The packaging can be opaque, but also transparent or translucent, and contains no propellants. The agents as contemplated herein are preferably applied by employing a spray device, which contains the cosmetic agents as contemplated herein and at least one propellant in a receptacle. A second subject matter of the invention is therefore a cosmetic product, comprising a) at least one cosmetic agent as contemplated herein and
b) at least one propellant.

Suitable receptacles for said cosmetic products include cylindrical vessels made of metal (aluminum, tinplate, capacity preferably maximum about 1,000 ml), protected and/or non-splintering glass or plastic (capacity preferably maximum 220 ml) and/or splintering glass or plastic (capacity preferably from about 50 to about 400 ml). Said receptacles also contain a valve, by employing which the cosmetic agent as contemplated herein can be removed in the form of mist, fumes, foam, powder, paste or liquid jet.

The cosmetic agent is the agent described under the first subject matter of the invention. Hence, all embodiments of the cosmetic agents of the first subject matter of the invention also apply, mutatis mutandis, to preferred embodiments of the cosmetic product. The cosmetic product as contemplated herein preferably contains the cosmetic agent in specific total quantities. Advantageous embodiments of this subject matter of the invention are therefore exemplified in that the cosmetic product contains the at least one cosmetic agent in a total quantity from about 5.0 to about 50 wt. %, preferably from about 5.0 to about 25 wt. %, more preferably from about 8.0 to about 20 wt. %, most preferably from about 10 to about 15 wt. %, relative to the total weight of the cosmetic product. The total weight of the cosmetic product is the weight of the cosmetic agent plus the weight of the propellant. The weight of the cosmetic product packaging, more particularly the receptacle with valve, is not however included.

According to this subject matter of the invention, the use of specific compounds as the propellant has proven advantageous. Therefore, it is preferable for the at least one propellant to be selected from the group of propane, propene, n-butane, iso-butane, iso-butene, n-pentane, pentene, iso-pentana, iso-pentene, methane, ethane, dimethylether, nitrogen, air, oxygen, laughing gas, 1,1,1,3-tetrafluorethane, heptafluoro-n-propane, perfluorethane, monochlordifluormethane, 1,1-difluorethane, tetrafluoropropene, as well as the mixtures thereof. Most preferred propellants are propane, n-butane, iso-butane, as well as the mixtures thereof, more particularly a mixture of propane and n-butane in the weight ratio of 15:85.

To ensure adequate sprayability of the cosmetic agents as contemplated herein, it is advantageous for the cosmetic product to contain the at least one propellant in a specific total quantity. Preferred embodiments are therefore exemplified in that the at least one propellant is contained in a total quantity from about 10 to about 95 wt. %, preferably from about 60 to about 95 wt. %, more preferably from about 70 to about 95 wt. %, most preferably from about 75 to about 95 wt. %, relative to the total weight of the cosmetic product. The total weight of the cosmetic product is the weight of the cosmetic agent plus the weight of the propellant. The weight of the cosmetic product packaging, more particularly the receptacle with valve, is not however included.

Most preferred embodiments K1 to K12 of the cosmetic product as contemplated herein are described below (all data in wt. %).

|  | K 1 | K 2 | K 3 | K 4 |
|---|---|---|---|---|
| Cosmetic agent[1] | 5.0-50 | 5.0-25 | 8.0-20 | 10-15 |
| Propellant | Ad 100 | Ad 100 | Ad 100 | Ad 100 |
|  | K 5 | K 6 | K 7 | K 8 |
| Cosmetic agent[1] | 5.0-50 | 5.0-25 | 8.0-20 | 10-15 |
| Propellant[2] | Ad 100 | Ad 100 | Ad 100 | Ad 100 |
|  | K 9 | K 10 | K 11 | K 12 |
| Cosmetic agent[1] | 5.0-50 | 5.0-25 | 8.0-20 | 10-15 |
| Propellant (E)[3] | Ad 100 | Ad 100 | Ad 100 | Ad 100 |

[1] Selected from one of the most preferred embodiments AF1 to AF156 mentioned under the first subject matter of the invention
[2] Selected from the group of propane, propene, n-butane, iso-butane, iso-butene, n-pentane, pentene, iso-pentane, iso-pentene, methane, ethane, dimethylether, nitrogen, air, oxygen, laughing gas, 1,1,1,3-tetrafluoroethane, heptafluoro-n-propane, perfluorethane, monochlordifluormethane, 1,1-difluorethane, tetrafluoropropene, as well as the mixtures thereof
[3] Selected from propane, n-butane, iso-butane, as well as the mixtures thereof The aforementioned cosmetic products K1 to K12 are readily sprayable. Moreover, said products do not lead to a premature clogging of the valves and can therefore be sprayed in their entirety. In addition, said products do not have any corrosive properties and have a long shelf life. Moreover, said products achieve an excellent deodorizing effect even in the absence of allergenic deodorizing perfume components.

With respect to other preferred embodiments of the cosmetic product, the statements made about the anhydrous composition as contemplated herein apply mutatis mutandis.

A third subject matter of the present disclosure is the use of the cosmetic agent as contemplated herein or of the cosmetic product as contemplated herein for reducing the body odor induced by perspiration.

The use of the cosmetic means as contemplated herein and/or the cosmetic product as contemplated herein creates, due to the combination of special cyclical alcohols of the Formula (I) and special menthyl compounds of the Formula (II) contained therein, a synergistic increase in the deodorizing effect, more particularly without the use of compounds with allergenic potential.

With respect to other preferred embodiments of use as contemplated herein, more particularly with respect to the used agent and/or the used product, the statements made about the cosmetic agent as contemplated herein and also about the cosmetic product as contemplated herein apply mutatis mutandis.

A final subject matter of the present disclosure is the use of a mixture of a) at least one alcohol of the Formula (I)

(I)

wherein
$R_1$ and $R_2$ denote, independently of one another, hydrogen, a linear $C_2$-$C_{10}$ hydroxyalkyl group or a branched $C_2$-$C_{10}$ hydroxyalkyl group, on condition that $R_1$ and $R_2$ do not both denote hydrogen,
b) at least one menthyl compound of the Formula (II)

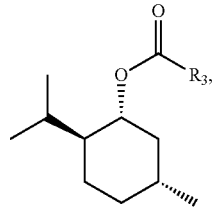

(II)

wherein
$R_3$ denotes a $C_1$-$C_4$-alkyl group, a $C_2$-$C_6$ hydroxyalkyl group or a pyrrolidone radical and to increase the odor-inhibiting effect of cosmetic agents.

The combination of the alcohol of the Formula (I) and the at least one menthyl compound of the Formula (II) creates a synergistic effect with respect to the deodorizing effect of cosmetic agents. Unlike deodorizing perfume components, said compounds also have no allergenic potential. Due to the slight intrinsic odor of said mixture, perfume-free cosmetic agents with an excellent deodorizing effect and no allergenic potential can therefore be formulated.

With respect to other preferred embodiments of the use as contemplated herein, more particularly with respect to the alcohol of the Formula (I), the menthyl compound of the Formula (II), as well as other constituents of the cosmetic agents, the statements made about the cosmetic agents as contemplated herein, about the cosmetic product as contemplated herein, and also about the method as contemplated herein, apply mutatis mutandis.

The following examples explain the present disclosure, without having any limiting effect:

EXAMPLES

1. Synergistic Effect with Respect to the Neutralization of Body Odor
The following anti-transpirant base suspension was used to determine the synergistic effect with respect to the neutralization of body odor (values in wt. %):

| Raw material | Quantity [wt. %] |
|---|---|
| Aluminum chlorohydrate | 33.3 |
| Triethyl citrate | 1.0 |
| Disteardimonium hectorite | 2.0 |
| Propylene carbonate | 3.5 |
| Isopropyl palmitate | 6.0 |
| Ethylhexyl palmitate | 7.0 |
| Cyclopentasiloxane | 46.9 |

Each of the following cyclical alcohols of the Formula (I) and/or menthyl compounds of the Formula (II) were added to said composition, wherein the total concentration of alcohol and/or menthyl compound in the suspension is 0.3 wt. % (all values in wt. %, relative to the used anti-transpirant suspension):

| No. | Alcohol of the Formula (I) | Menthyl compound of the Formula (II) | Quantity [wt. %] |
|---|---|---|---|
| 1 | 2-methyl-5-cyclohexylpentanol[1)] | — | 0.3 |
| 2 | 1-cyclohexylethanol[2)] | — | 0.3 |
| 3 | Dimethylolcyclohexane[3)] | — | 0.3 |
| 4 | — | Menthyl acetate[4)] | 0.3 |
| 5 | — | Menthyllactate[5)] | 0.3 |
| 6 | — | Pyroglutamic acid-menthylester[6)] | 0.3 |
| 7* | 2-methyl-5-cyclohexylpentanol[1)] | Menthyl acetate[4)] | 0.15 in each case |
| 8* | 1-cyclohexylethanol[2)] | 1-cyclohexylethanol[2)] | 0.15 in each case |
| 9* | 1-cyclohexylethanol[2)] | Menthyllactate[5)] | 0.15 in each case |
| 10* | 1-cyclohexylethanol[2)] | Pyroglutamic acid-menthylester[6)] | 0.15 in each case |
| 11* | Dimethylolcyclohexane[3)] | Menthyllactate[5)] | 0.15 in each case |

[1)] $R_1 = H$, $R_2 = $ *—$(CH_2)_3$—$CH(CH_3)$—$CH_2$—OH
[2)] $R_1 = H$, $R_2 = $ *—$CH(CH_3)$—OH
[3)] $R_1$ and $R_2$ both denote *—$CH_2$—OH
[4)] $R_3 = $ *—$CH_3$
[5)] $R_3 = $ *—$CH(OH)$—$CH_3$
[6)] $R_3 = $ pyrrolidone radical
*as contemplated herein Said suspensions, each with a weight ratio of 15:85, were then placed in aerosol cans with a propellant mixture of propane and n-butane (weight ratio 15:85). Specimens No. 1 to 11 were each applied to the left armpit, the anti-transpirant base suspension to the right armpit. 24 hours after application, the body odor on the worn T-shirt on the left armpit (treated with specimens No. 1 to 11) were compared to the body odor of the right armpit (treated with anti-transpirant base suspension) by trained persons. The following rating scale was used: 0=no difference between specimen No. 1 to 11 and anti-transpirant base suspension; +=body odor reduced compared to anti-transpirant base suspension; ++=body odor no longer discernible on the T-shirt.

The following results for body odor were obtained:

| Specimen No. | Body odor |
|---|---|
| 1 | + |
| 2 | + |
| 3 | 0 |
| 4 | + |
| 5 | 0 |
| 6 | 0 |

-continued

| Specimen No. | Body odor |
|---|---|
| 7* | ++ |
| 8* | ++ |
| 9* | ++ |
| 10* | ++ |
| 11* | + |

*as contemplated herein

Indeed, a deodorizing effect is achieved solely through the use of 2-methyl-5-cyclohexylpentanol, 1-cyclohexylethanol and menthylacetate. Surprisingly, however, this effect was able to be synergistically increased through the combination of a special menthyl compound of the Formula (II) and/or with a special cyclical alcohol of the Formula (I). Moreover, the mixtures as contemplated herein in the used concentrations have only a slight intrinsic odor. Therefore, the use of perfume components having allergenic potential is not required, and this has no negative impact on the excellent and long-lasting deodorizing effect.

2. Formulations

Sprayable Anti-Transpirant Suspension (all Quantities in Wt. %)

| | 1.1 | 1.2 | 1.3 | 1.4 | 1.5 | 1.6 | 1.7 | 1.8 | 1.9 |
|---|---|---|---|---|---|---|---|---|---|
| 1-cyclohexylethanol | 0.15 | — | — | 0.15 | — | 0.15 | 0.15 | 0.15 | 0.15 |
| 2-methyl-5-cyclohexylpentanol | — | 0.15 | — | — | — | — | — | — | — |
| Dimethylolcyclohexane | — | — | — | — | 0.15 | — | — | — | — |
| Menthylacetate | 0.15 | 0.15 | — | — | — | — | 0.15 | — | 0.21 |
| Menthyllactate | — | — | — | 0.15 | 0.15 | — | — | 0.15 | — |
| Pyroglutamic acid-menthylester | — | — | — | — | — | 0.15 | — | — | — |
| Triethyl citrate | 1.0 | 1.0 | 1.0 | 1.0 | 1.0 | 1.0 | 1.0 | 1.0 | 1.0 |
| Aluminum chlorohydrate | 33.3 | 33.3 | 33.3 | 33.3 | 33.3 | 33.3 | 33.3 | 33.3 | 33.3 |
| Ethylhexyl palmitate | 7.0 | 7.0 | 7.0 | 7.0 | 7.0 | 7.0 | 7.0 | 7.0 | 7.0 |
| Isopropyl myristate | 6.0 | 6.0 | 6.0 | 6.0 | 6.0 | 6.0 | 6.0 | 6.0 | 6.0 |

-continued

|  | 1.1 | 1.2 | 1.3 | 1.4 | 1.5 | 1.6 | 1.7 | 1.8 | 1.9 |
|---|---|---|---|---|---|---|---|---|---|
| Disteardimonium hectorite | 2.0 | 2.0 | 2.0 | 2.0 | 2.0 | 2.0 | 2.0 | 2.0 | 2.0 |
| Propylene carbonate | 3.5 | 4.0 | 0.9 | 0.9 | 1.5 | 2.0 | 2.5 | 3.0 | 4.5 |
| Perfume | — | — | — | — | — | — | 3.0 | 3.0 | 6.0 |
| Cyclopentasiloxane | Ad 100 | Ad 100 | Ad 100 | Ad 100 | Ad 100 | Ad 100 | Ad 100 | Ad 100 | Ad 100 |

Compositions 1.1 to 1.9, each with the weight ratio of 15:85, are placed in aerosol cans with a propellant mixture of propane and n-butane (in a weight ratio of 15:85). All compositions lead to an excellent and long-lasting deodorizing effect.

Sprayable Deodorant Compositions (Values in Wt. %)

|  | 2.1 | 2.2 | 2.3 | 2.4 | 2.5 | 2.6 | 2.7 | 2.8 | 2.9 |
|---|---|---|---|---|---|---|---|---|---|
| 1-cyclohexylethanol | 0.15 | — | — | 0.15 | — | 0.15 | 0.15 | 0.15 | 0.15 |
| 2-methyl-5-cyclohexylpentanol | — | 0.15 | — | — | — | — | — | — | — |
| Dimethylolcyclohexane | — | — | — | — | 0.15 | — | — | — | — |
| Menthylacetate | 0.15 | 0.15 | — | — | — | — | 0.15 | — | 0.21 |
| Menthyllactate | — | — | — | 0.15 | 0.15 | — | — | 0.15 | — |
| Pyroglutamic acid-menthylester | — | — | — | — | — | 0.15 | — | — | — |
| Triethyl citrate | 6.0 |  |  |  |  |  |  |  |  |
| Ethylhexylglycerine | 0.9 |  |  |  |  |  |  |  |  |
| Phenoxyethanol | 0.25 |  |  |  |  |  |  |  |  |
| Perfume | 3.0 | 3.0 | 3.0 | 3.0 | 3.0 | 3.0 | — | 0.5 | 6.0 |
| Ethanol 96% | Ad 100 | Ad 100 | Ad 100 | Ad 100 | Ad 100 | Ad 100 | Ad 100 | Ad 100 | Ad 100 |

Compositions 2.1 to 2.9, each with the weight ratio of 15:85, are placed in aerosol cans with a propellant mixture of propane and n-butane (in a weight ratio of 15:85). All compositions lead to an excellent and long-lasting deodorizing effect.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. Cosmetic agent comprising, relative to the total weight thereof, a) at least one alcohol of the Formula (I)

(I)

wherein $R_1$ and $R_2$ denote, independently of one another, hydrogen, a linear $C_2$-$C_{10}$ hydroxyalkyl group or a branched $C_2$-$C_{10}$ hydroxyalkyl group, on condition that $R_1$ and $R_2$ do not both denote hydrogen, b) at least one menthyl compound of the Formula (II)

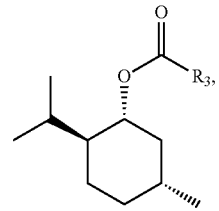

(II)

wherein $R_3$ denotes a $C_1$-$C_4$-alkyl group, a $C_2$-$C_6$ hydroxyalkyl group or a pyrrolidone radical and c) at least one antiperspirant compound and/or at least one deodorant active ingredient, wherein the cosmetic agent contains no additional scents or mixtures thereof selected from the group of perfume oils, perfumes, or perfume oil constituents, wherein the at least one alcohol of the Formula (I) is selected from the group of 2-methyl-5-cyclohexylpentanol, 1-cyclohexylethanol, dimethylolcyclohexane, or combinations thereof, and wherein the at least one menthyl compound of the Formula (II) is selected from the group of menthyl acetate, menthyllactate, pyroglutamic acid-menthylester, or combinations thereof, and wherein the at least one alcohol of the Formula (I) is present in a total quantity of about 0.15 wt. % and the at least one menthyl compound of the Formula (II) is present in a total quantity of about 0.15 wt. %, in each case relative to the total weight of the cosmetic agent.

2. Cosmetic agent according to claim 1, wherein the cosmetic agent is free of antiperspirant compounds.

3. Cosmetic product, comprising
a) at least one cosmetic agent according to claim 1, and
b) at least one propellant.

4. A method comprising using the cosmetic agent according to claim 1 for reducing the body odor induced by perspiration.

* * * * *